US012765954B2

(12) United States Patent
Liu et al.

(10) Patent No.: US 12,765,954 B2
(45) Date of Patent: Oct. 20, 2026

(54) TRACING DEVICE AND SELF-COMPENSATION TRACKING METHOD OF ORTHOPEDIC SURGERY ROBOT

(71) Applicant: NANJING PERLOVE MEDICAL EQUIPMENT CO., LTD, Nanjing (CN)

(72) Inventors: Jinhu Liu, Nanjing (CN); Yingqin Shi, Nanjing (CN)

(73) Assignee: NANJING PERLOVE MEDICAL EQUIPMENT CO., LTD, Nanjing (CN)

( * ) Notice: Subject to any disclaimer, the term of this patent is extended or adjusted under 35 U.S.C. 154(b) by 11 days.

(21) Appl. No.: 18/844,405

(22) PCT Filed: Oct. 17, 2022

(86) PCT No.: PCT/CN2022/125645

§ 371 (c)(1),
(2) Date: Sep. 6, 2024

(87) PCT Pub. No.: WO2024/000931

PCT Pub. Date: Jan. 4, 2024

(65) Prior Publication Data

US 2025/0186146 A1 Jun. 12, 2025

(30) Foreign Application Priority Data

Jun. 28, 2022 (CN) ......................... 202210749345.1

(51) Int. Cl.
*A61B 34/35* (2016.01)
*A61B 34/20* (2016.01)

(52) U.S. Cl.
CPC .............. *A61B 34/35* (2016.02); *A61B 34/20* (2016.02); *A61B 2034/2055* (2016.02); *A61B 2034/2065* (2016.02)

(58) Field of Classification Search
CPC . A61B 34/35; A61B 34/20; A61B 2034/2055; A61B 2034/2065;

(Continued)

(56) References Cited

U.S. PATENT DOCUMENTS

2017/0020613 A1* 1/2017 Kang ..................... A61B 34/76
2017/0119411 A1* 5/2017 Shah ................ A61B 17/32002

(Continued)

*Primary Examiner* — Adam R Mott
*Assistant Examiner* — Sagar Kc
(74) *Attorney, Agent, or Firm* — CBM PATENT CONSULTING, LLC

(57) ABSTRACT

Disclosed are a tracing device and self-compensation tracking method of an orthopedic surgery robot. The tracing device comprises a rigid body support, and a tracer is arranged on the rigid body support; and the method comprises the following steps of: acquiring a corresponding reference point cloud in an optical tracker coordinate system, and recording basic pose information of the tracing device in an optical tracker; calculating a pose conversion relation between a coordinate system where the robot is located and the optical tracker coordinate system, and determining the pose conversion relation; and in a robot navigation system, detecting a pose change of a tracking device in real time, and updating a conversion relation from an image coordinate system to the robot coordinate system in real time, so as to control effective execution of the robot.

7 Claims, 4 Drawing Sheets

(58) Field of Classification Search
CPC . A61B 2090/3764; A61B 34/30; A61B 34/10; A61B 2034/107; A61B 2034/108; G06T 7/73; G06T 19/003; G06T 2207/10028
See application file for complete search history.

(56) References Cited

U.S. PATENT DOCUMENTS

| | | | | |
|---|---|---|---|---|
| 2018/0049825 | A1* | 2/2018 | Kwon .................... | A61B 90/14 |
| 2020/0035122 | A1* | 1/2020 | Abbott .................... | G06T 19/20 |
| 2022/0031398 | A1* | 2/2022 | Zheng .................... | A61B 34/37 |
| 2024/0065771 | A1* | 2/2024 | Zhang .................... | A61B 34/25 |

* cited by examiner

TRACING DEVICE AND SELF-COMPENSATION TRACKING METHOD OF ORTHOPEDIC SURGERY ROBOT

TECHNICAL FIELD

The present invention relates to a robot tracing device and tracking method, and is particularly a tracing device and self-compensation tracking method of an orthopedic surgery robot.

BACKGROUND

In recent years, navigational positioning system technology has become the mainstream of innovation in the medical field, especially the innovative application of robot technology, which has improved the safety and effectiveness of orthopedic surgery. A basic function of an orthopedic surgery robot system is to process and display an image provided by medical imaging equipment through a computer, and to finally control the robot to realize surgery positioning safely and effectively in combination with an optical tracker.

In an actual clinical process, due to a limited operating space, the robot or the optical tracker in the system needs to constantly change its pose due to clinical needs, which changes a previous relative conversion relation between systems, thus causing a final moving position deviation of the robot.

SUMMARY

Object of invention: the technical problem to be solved by the present invention is to provide a tracing device and self-compensation tracking method of an orthopedic surgery robot aiming at the defects in the prior art.

In order to solve the above technical problem, the present invention discloses a tracing device and self-compensation tracking method of an orthopedic surgery robot.

A tracing device of an orthopedic surgery robot comprises a rigid body support, wherein a tracer is arranged on the rigid body support.

The rigid body support comprises a movable joint and a connecting rod, and a position and a pose of the tracer are adjusted and fixed through the joint.

The tracer comprises a registration point supporting frame and a registration point; and the registration points are arranged around the registration point supporting frame in a coplanar and non-collinear manner.

Not less than three registration points are provided.

The tracing device further comprises a connecting component for connecting with the outside.

The rigid body support comprises a first joint, a second joint, a third joint, a fourth joint, a fifth joint, a first connecting rod, a second connecting rod, a third connecting rod, a fourth connecting rod and a fifth connecting rod;

wherein, the first joint connects the first connecting rod with the connecting component, and the first joint is a 360° rotating joint;

the second joint connects the first connecting rod with the second connecting rod, and the second joint is a turning joint;

the third joint connects the second connecting rod with the third connecting rod, and the third joint is a turning joint;

the fourth joint connects the third connecting rod with the fourth connecting rod, and the fourth joint is a 360° rotating joint;

the fifth joint connects the fourth connecting rod with the fifth connecting rod, and the fifth joint is a turning joint; and the fifth connecting rod is connected with a mounting interface for mounting the tracer.

An orthopedic surgery robot comprises a host machine and an orthopedic surgery manipulator, wherein a tracer is arranged on the orthopedic surgery manipulator, the rigid body support is arranged on the host machine or the orthopedic surgery manipulator, and the tracer is arranged on the rigid body support.

A self-compensation tracking method of an orthopedic surgery robot comprises a non-transitory computer readable medium operable on a computer with memory for the self-compensation tracking method, and comprising program instructions for executing the following steps of:

step 1: starting an optical tracker;

step 2: placing a tracing device in a visual field of the optical tracker, acquiring and saving corresponding basic pose information T_p_old of the tracing device in the optical tracker, and simultaneously acquiring a reference point cloud R_pionts of the orthopedic surgery robot and a reference point cloud N_Points of the optical tracker;

step 3: acquiring 3D navigation image data which meet a precision of an orthopedic surgery robot navigation system and related position information collected by 3D imaging equipment;

step 4: calculating a conversion relation M_n between an optical tracker coordinate system and a 3D navigation image data coordinate system;

step 5: calculating acquisition moments of the reference point cloud R_pionts of the orthopedic surgery robot and the reference point cloud N_points of the optical tracker, and a pose conversion relation M_old between the optical tracker coordinate system and an orthopedic surgery robot coordinate system; tracking corresponding pose information T_p_new of a current tracing device in the optical tracker in real time, and calculating a conversion relation M_t_p between the pose information and basic pose information T_p_old, and then, in combination with the pose conversion relation M_old, calculating and updating a pose conversion relation M_new between a current optical tracker coordinate system and the orthopedic surgery robot coordinate system;

step 6: according to the obtained pose conversion relation M_new in the step 5, in combination with the obtained pose conversion relation M_n in the step 4, converting a pose in the 3D navigation image data coordinate system into a pose in the robot coordinate system, and sending designated pose information to the orthopedic surgery robot, so as to control the orthopedic surgery robot to move to a corresponding position; and step 7: calculating an error $\delta$ between a real-time display of a pose of a current orthopedic surgery robot in a 3D navigation image and an actual planning point to verify whether the moving pose of the current orthopedic surgery robot meets a precision requirement.

The step 7 comprises:

step 7-1: acquiring a current pose of the orthopedic surgery robot through the optical tracker;

step 7-2: according to the conversion relation M_n between the optical tracker coordinate system and the 3D navigation image coordinate system, converting the current pose of the orthopedic surgery robot to the 3D navigation image coordinate system to display; and step 7-3: calculating a difference between coordinates of the moving pose of the current orthopedic surgery robot in the 3D navigation image and coordinates of a target moving pose during pre-planning in the 3D navigation image.

The acquisition moments of the reference point cloud R_pionts of the orthopedic surgery robot and the reference point cloud N_points of the optical tracker are calculated in the step 5, and the pose conversion relation M_old between the optical tracker coordinate system and the orthopedic surgery robot coordinate system is calculated by an iterative closest point algorithm, which is namely an ICP algorithm, or a matrix singular value decomposition algorithm.

Beneficial Effects

According to the present invention, the pose change of the robot coordinate system or the optical tracker coordinate system can be detected in real time and optimized in time, which avoids an influence of the pose change of the robot coordinate system or the optical tracker on an execution precision of the orthopedic surgery robot system in clinic, and ensures the stability and reliability of the system precision, thus having an extremely high application value in an application of the orthopedic surgery robot system.

BRIEF DESCRIPTION OF THE DRAWINGS

The present invention is further described in detail hereinafter with reference to the drawings and specific embodiments, and the advantages of the above and/or other aspects of the present invention will be clearer.

DETAILED DESCRIPTION

The technical solutions of the present invention are clearly and completely described hereinafter with reference to the drawings in the present invention.

Figure 1:
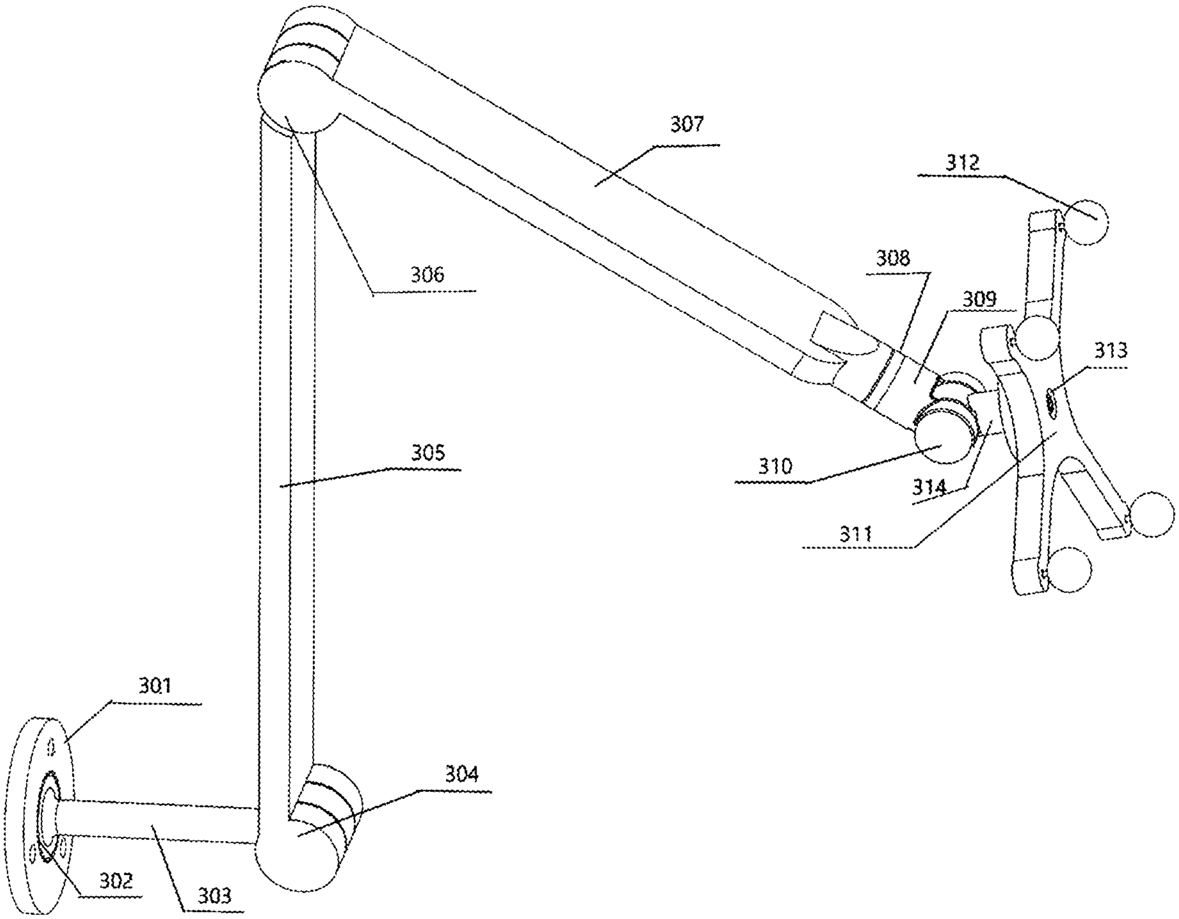
FIG. 1 is a schematic structural diagram of a tracing device of an orthopedic surgery robot according to the present invention.

The present invention provides a tracing device of an orthopedic surgery robot, as shown in FIG. 1, which is a schematic diagram of the tracing device of the orthopedic surgery robot according to the present invention. The tracing device of the orthopedic surgery robot comprises a rigid body support, which comprises a first joint 302, a second joint 304, a third joint 306, a fourth joint 308, a fifth joint 310, a first connecting rod 303, a second connecting rod 305, a third connecting rod 307, a fourth connecting rod 309 and a fifth connecting rod 314; a tracer, which comprises a registration point supporting frame 311, at least three coplanar and non-collinear registration points 312 and a mounting interface 313; and a connecting component 301.

Figure 2:
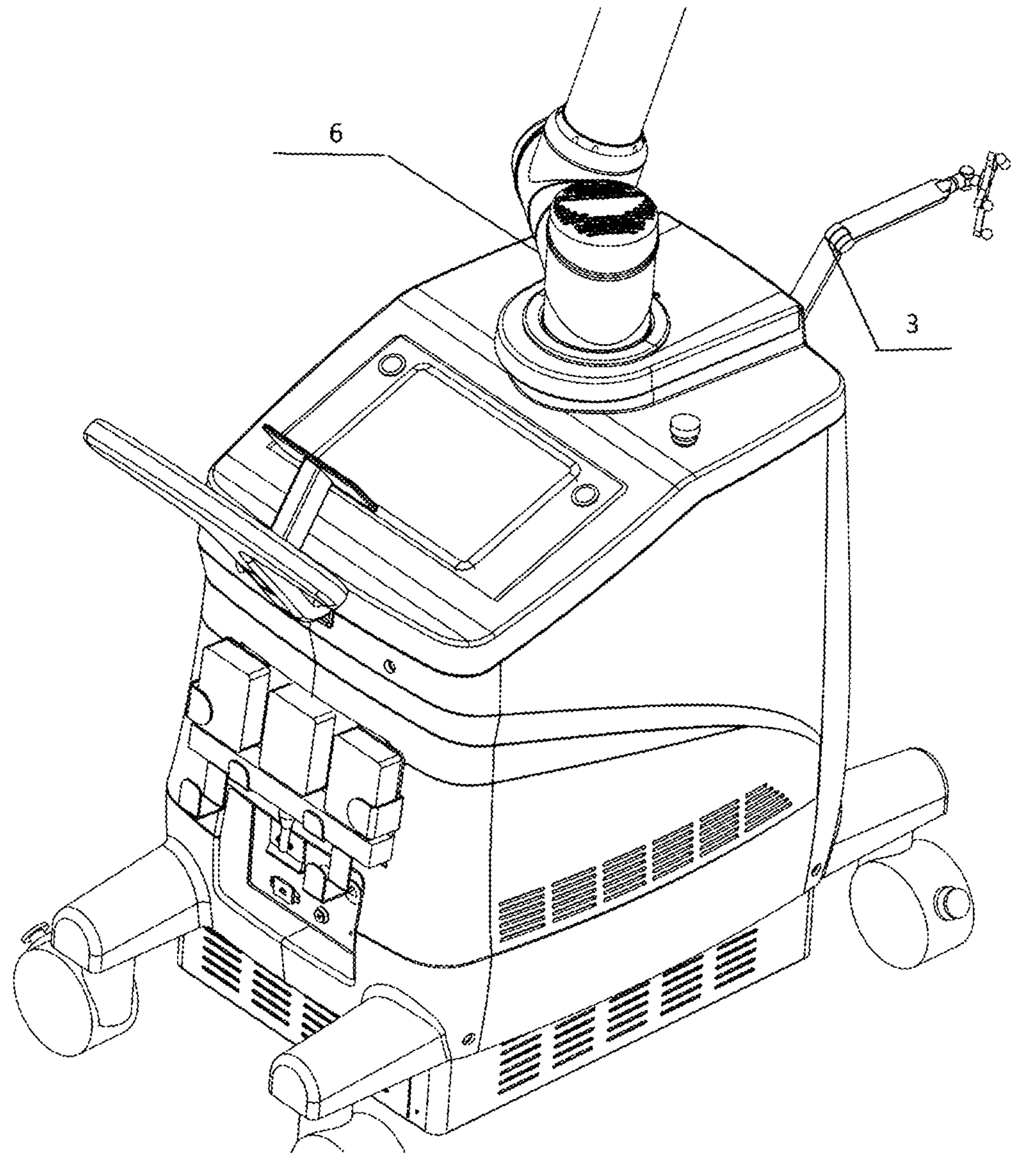
FIG. 2 is a mounting diagram of the tracing device of the orthopedic surgery robot according to the present invention.

As shown in FIG. 2, which is a mounting diagram of the tracing device of the orthopedic surgery robot, a mounting position is arranged on the premise of not affecting a clinical surgery. According to a mounting design, the tracing device is ingeniously integrated with a base of a robot 6 through the connecting component 301, which is simple and stable, and ensures that there is no relative pose change, thus ensuring the system precision. According to a position of a current system or a surgery space, the joint may be properly stretched or rotated, so that the tracer is located in a proper position, without affecting the movement of the orthopedic surgery robot 6, and sufficient space is left for any action of the orthopedic surgery robot 6.

Figure 3:
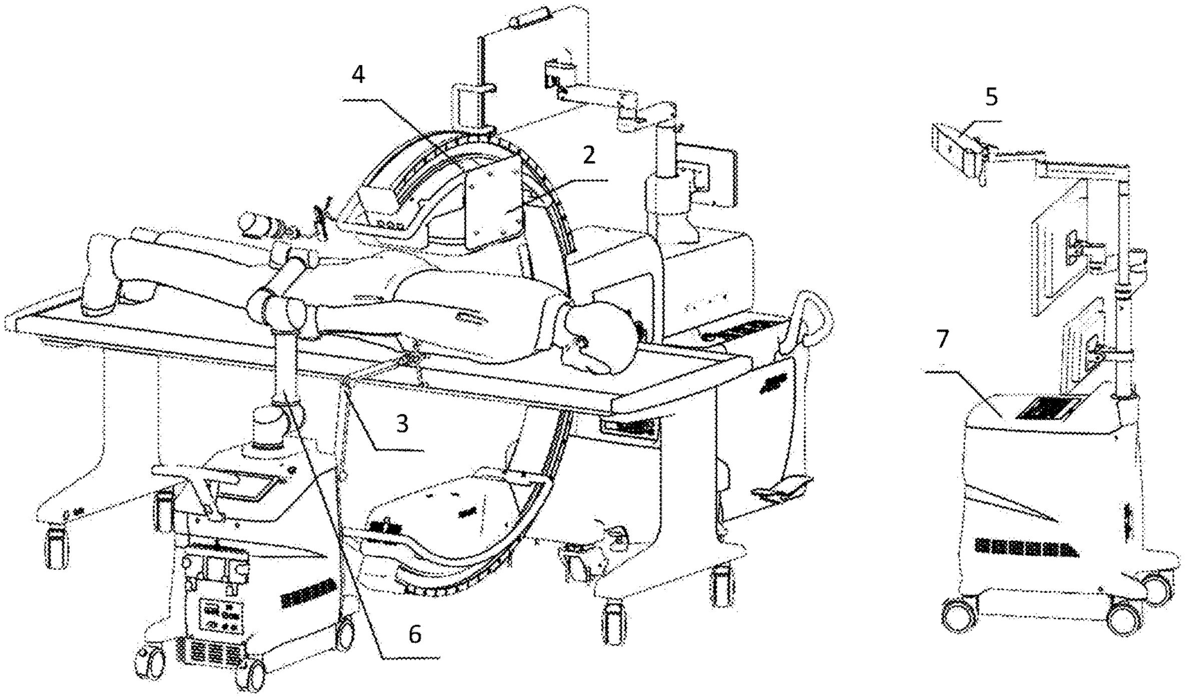
FIG. 3 is a structural diagram of a system according to the present invention.

The present invention provides a tracking device system of an orthopedic surgery robot, as shown in FIG. 3, which comprises a three-dimensional C-arm 4, an optical tracker 5, an orthopedic surgery robot 6, a workstation 7, an integrated registration device 2 and a tracing device 3.

The tracing device comprises a rigid body support; a tracer; and a connecting component, which are convenient to be disassembled and assembled.

The rigid body support has five self-balancing joints and five connecting rods. Considering the stability and functional availability of structure, a joint 1 should be able to rotate infinitely by 360°, and the overall rotation of the support should be carried out to achieve the purpose of direction adjustment; a joint 4 should be able to rotate infinitely by 360°, and a joint 5 and the tracer may be rotated integrally to achieve the purpose of direction adjustment; the joint 5 may independently adjust a pose of the tracer by turning; other joints may be turned by less than 360°, and may be properly stretched and rotated according to position needs of a current system, so as to achieve the purpose of adjusting the pose of the tracer; and a tail end connecting rod is provided with a mounting interface fixedly connected with the tracer.

The tracer comprises a registration point support frame, at least three coplanar and non-collinear registration points and the mounting interface, and a geometric structure of the registration points must meet an identification requirement of the optical tracker in the orthopedic surgery robot; and a material selection of the tracer must be consistent with that of the optical tracker in the orthopedic surgery robot, wherein if the optical tracker is based on an optical principle, a passive luminous tracer must be used, and if the optical tracker is based on an electromagnetic identification principle, an active luminous tracer must be used. The tracer is mounted on the tail end connecting rod of the rigid body support, and the fixation must be firm, without loosening or rotating, otherwise a navigation precision of the orthopedic surgery robot system will be affected.

Figure 4:
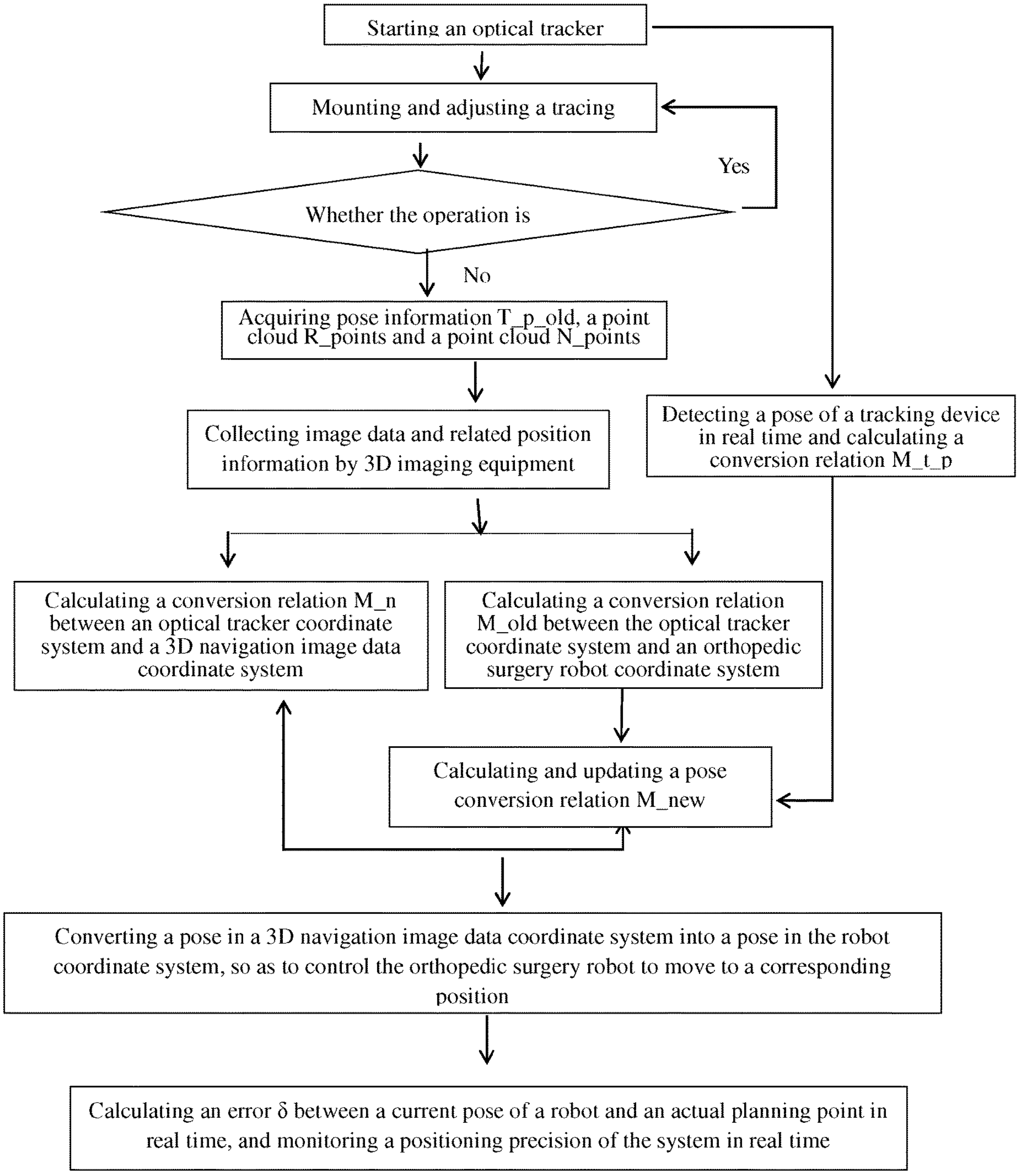
FIG. 4 is a flow chart of a method according to the present invention.

The present invention provides a self-compensation tracking method of an orthopedic surgery robot, as shown in FIG. 4, which comprises a non-transitory computer readable medium operable on a computer with memory for the self-compensation tracking method, and comprising program instructions for executing the following steps of:

The tracing device 3 is mounted on the base of the orthopedic surgery robot 6, and the mounting position has a fixed structure with the robot 6, so as to meet the mounting requirement, as shown in FIG. 2.

According to an operation principle and a corresponding geometric structure of the orthopedic surgery robot 6, pose information of a specific tip with the tracer at a tail end of the orthopedic surgery robot 6 in different planes is recorded, which is a reference point cloud R_p of the robot 6, and there are at least five or more reference point clouds.

The optical tracker 5 and the orthopedic surgery robot 6 are started, the tracing device 3 and the specific tip with the tracer at the tail end of the orthopedic surgery robot 6 are ensured to be within a visual field of the optical tracker 5, the reference point cloud N_p of the optical tracker 5 is ensured to be precisely acquired, and corresponding basic pose information T_p_ of the tracing device 3 in the optical tracker 5 is saved simultaneously.

The three-dimensional C-arm 4 is started, 3D image data are collected and sent, and the workstation 7 receives and displays the 3D image data and related configuration information. According to an orthopedic surgery robot system principle, a conversion relation M_n between an optical tracker 5 coordinate system and an image coordinate system is calculated by using pose information of an integrated registration device 2.

In combination with the step (3), by applying an ICP algorithm and an SVD algorithm, the workstation 7 calculates a pose conversion relation M_old between the optical tracker 5 coordinate system and an orthopedic surgery robot 6 coordinate system when the reference point cloud is acquired. The optical tracker 5 detects pose information of the tracing device 3 in real time, and updates a pose conversion relation M_new between the optical tracker 5 coordinate system and the orthopedic surgery robot 6 coordinate system in real time.

The workstation 7 pre-plans through the image, and specifies final pose information of the movement of the orthopedic surgery robot 6. In combination with the step (4) and the step (5), a conversion relation between an image coordinate system and the orthopedic surgery robot 6 coordinate system is calculated, so as to control the orthopedic surgery robot 6 to move to a target position.

The workstation 7 calculates an error δ between a pose of a current orthopedic surgery robot 6 and an actual planning point in real time, so as to ensure that the moving pose of the orthopedic surgery robot 6 meets a system precision requirement in real time.

ICP algorithm: according to certain constraints, optimal matching parameters R and t are calculated, so that the following error function is minimized, $$E(R, t) = \frac{1}{n}\sum_{i=1}^{n}\|p2_i - (Rp1_i + t)\|^2$$

wherein, n is a number of closest point pairs, $p2_i$ is one point in a target point cloud p2, $p1_i$ is a closet point corresponding to $p2_i$ in a source point cloud p1, R is a rotation matrix, and t is a translation vector.

Algorithm implementation steps comprise:

(1) taking a point set $p2_i \in p2$ from the target point cloud p2.

(2) finding out a corresponding point set $p1_i \in p1$ from the source point cloud p1, so that $\|p1_i - p2_i\| = \min$ (3) calculating the rotation matrix R and the translation matrix t to minimize the error function;

(4) performing rotation and translation transformation on $p1_i$ by using the rotation matrix R and the translation matrix t obtained in the previous step to obtain a new corresponding point set $p' = \{p'_i = Rp1_i + t, p1_i \in p1\}$.

(5) calculating an average distance from p' to the corresponding point set p1

$$d = \frac{1}{n}\sum_{i=1}^{n}\|p'_i - p1_i\|^2$$

and (6) if d is less than a certain given threshold or greater than a preset maximum number of iterations, stopping the iterative calculation, and otherwise, returning to the step 2, until convergence conditions are met.

The present invention provides an idea and a method for a tracing device and self-compensation tracking method of an orthopedic surgery robot, with many methods and ways to realize the technical solution specifically. Those described above are merely the preferred embodiments of the present invention, and it should be pointed out that those of ordinary skills in the art may further make improvements and decorations without departing from the principle of the present invention, and these improvements and decorations should also be regarded as the scope of protection of the present invention. All the unspecified components in the embodiments can be realized by the prior art.

What is claimed is:

1. A self-compensation tracking method of an orthopedic surgery robot, comprising a non-transitory computer readable medium operable on a computer with memory for the self-compensation tracking method, and comprising program instructions for executing the following steps of:

acquiring corresponding basic pose information of a tracing device in an optical tracker, a reference point cloud of the orthopedic surgery robot and a reference point cloud of the optical tracker;

acquiring 3D navigation image data and position information of the optical tracker; calculating a conversion relation between an optical tracker coordinate system and a 3D navigation image data coordinate system of a 3D imaging equipment;

calculating acquisition times of the reference point clouds of the orthopedic surgery robot and the reference point cloud of the optical tracker, and a pose conversion relation between the optical tracker coordinate system and an orthopedic surgery robot coordinate system, wherein, according to positioning coordinates and pose data of a tracer for positioning compensation, in combination with positioning coordinates and pose data of the orthopedic surgery robot and the optical tracker, the pose conversion relation between the optical tracker coordinate system and the orthopedic surgery robot coordinate system is calculated by an iterative closest point algorithm, which is namely an ICP algorithm, or a matrix singular value decomposition algorithm;

tracking corresponding pose information of a current tracing device in the optical tracker in real time, and calculating a conversion relation between the pose information and the basic pose information, and then, in combination with the pose conversion relation between the optical tracker coordinate system and the orthopedic surgery robot coordinate system, calculating and updating a pose conversion relation between a current optical tracker coordinate system and the orthopedic surgery robot coordinate system; and according to the updated pose conversion relation between the current optical tracker coordinate system and the orthopedic surgery robot coordinate system, in combination with the conversion relation between the optical tracker coordinate system and the 3D navigation image data coordinate system, converting a pose in the 3D navigation image data coordinate system into a pose in the robot coordinate system, and sending the pose to the orthopedic surgery robot, so as to control the orthopedic surgery robot to move to a corresponding position.

2. The self-compensation tracking method of the orthopedic surgery robot according to claim 1, wherein an error δ between a real-time display of a pose of a current orthopedic surgery robot in a 3D navigation image and an actual planning point is calculated to verify whether the moving pose of the current orthopedic surgery robot meets a precision requirement.

3. The self-compensation tracking method of the orthopedic surgery robot according to claim 2, wherein a method for calculating the error between the real-time display of the pose of the current orthopedic surgery robot in the 3D navigation image and the actual planning point comprises the following steps of:

acquiring a current pose of the orthopedic surgery robot through the optical tracker;

according to the conversion relation between the optical tracker coordinate system and the 3D navigation image data coordinate system, converting the current pose of the orthopedic surgery robot to the 3D navigation image data coordinate system to display; and calculating a difference between coordinates of the moving pose of the current orthopedic surgery robot in the 3D navigation image and coordinates of a target moving pose during pre-planning in the 3D navigation image.

4. The self-compensation tracking method of the orthopedic surgery robot according to claim 1, wherein the tracing device comprises a rigid body support, wherein the tracer for positioning compensation is arranged on the rigid body support.

5. The self-compensation tracking method of the orthopedic surgery robot according to claim 4, wherein the rigid body support comprises a movable joint and a connecting rod, and a position and a pose of the tracer are adjusted and fixed through the movable joint and the connecting rod.

6. The self-compensation tracking method of the orthopedic surgery robot according to claim 5, wherein the tracer comprises a registration point supporting frame (311) and registration points (312); the registration points (312) are arranged around the registration point supporting frame (311) in a coplanar and non-collinear manner; and not less than three registration points (312) are provided.

7. The self-compensation tracking method of the orthopedic surgery robot according to claim 6, comprising a connecting component (301) for connecting with the outside, wherein the rigid body support comprises a first joint (302), a second joint (304), a third joint (306), a fourth joint (308), a fifth joint (310), a first connecting rod (303), a second connecting rod (305), a third connecting rod (307), a fourth connecting rod (309) and a fifth connecting rod (314);

wherein, the first joint (302) connects the first connecting rod (303) with the connecting component (301), and the first joint (302) is a 360° rotating joint;

the second joint (304) connects the first connecting rod (303) with the second connecting rod (305), and the second joint (304) is a turning joint;

the third joint (306) connects the second connecting rod (305) with the third connecting rod (307), and the third joint (306) is a turning joint;

the fourth joint (308) connects the third connecting rod (307) with the fourth connecting rod (309), and the fourth joint (308) is a 360° rotating joint;

the fifth joint (310) connects the fourth connecting rod (309) with the fifth connecting rod (314), and the fifth joint (310) is a turning joint; and the fifth connecting rod (314) is connected with a mounting interface (313) for mounting the tracer.

* * * * *